United States Patent [19]

Seither et al.

[11] 3,932,522
[45] Jan. 13, 1976

[54] MANUFACTURE OF FORMALDEHYDE

[75] Inventors: Karl Seither; Guenther Matthias, both of Ludwigshafen; Hans Diem, Mannheim; Oskar Hussy; Hans Haas, both of Ludwigshafen, all of Germany

[73] Assignee: Badische Anilin- & Soda-Fabrik Aktiengesellschaft, Ludwigshafen (Rhine), Germany

[22] Filed: Mar. 22, 1972

[21] Appl. No.: 236,971

[30] Foreign Application Priority Data

Mar. 25, 1971 Germany............................. 2114370

[52] U.S. Cl. .......................................... 260/603 HF
[51] Int. Cl.² ........................................... C07C 47/04
[58] Field of Search................................ 260/603 HF

[56] References Cited
UNITED STATES PATENTS

| 1,213,740 | 1/1917  | Calvert ............................ | 260/603    |
| 2,436,287 | 2/1948  | Brendyke......................... | 260/603    |
| 2,662,911 | 12/1953 | Dorschner et al. ............. | 260/603    |
| 2,888,140 | 8/1958  | Hebert............................. | 260/603 HF X |

FOREIGN PATENTS OR APPLICATIONS

| 1,135,476 | 12/1968 | United Kingdom ........ | 260/603 HF |
| 1,903,197 | 8/1970  | Germany...................... | 260/603 R  |
| 1,576,568 | 6/1969  | France......................... | 260/603    |
| 1,131,380 | 10/1968 | United Kingdom.......... | 260/603    |

OTHER PUBLICATIONS

Brown et al., Unit Operations, 1950, p. 120, John Wiley & Sons.

*Primary Examiner*—James O. Thomas, Jr.
*Assistant Examiner*—R. H. Liles
*Attorney, Agent, or Firm*—Johnston, Keil, Thompson & Shurtleff

[57] ABSTRACT

The manufacture of formaldehyde by oxidative dehydrogenation of crude methanol in the presence of a silver catalyst, the crude methanol being caused to impinge against baffle plates before the reaction takes place, the impurities which separate at the baffle plates being collected. The formaldehyde manufactured by the process of the invention is valuable as a disinfectant, tanning agent, reducing agent and intermediate in the manufacture of synthetic resins, adhesives and plastics.

9 Claims, No Drawings

MANUFACTURE OF FORMALDEHYDE

This invention relates to a process for the manufacture of formaldehyde by oxidative dehydrogenation of crude methanol in the presence of a silver catalyst, the crude methanol being caused to impinge against baffle plates before the reaction takes place, the impurities which separate at said baffle plates being collected.

In Ullmann's Encyklopaedie der technischen Chemie, Vol. 7, pp. 659 et seq., there are described various processes for the manufacture of formaldehyde by oxidative dehydrogenation of methanol in the presence of a silver catalyst at elevated temperature. The starting material used is pure methanol obtained from crude methanol by fractional distillation. Crude methanol may vary in composition according to its manufacturing process (Ullmann's Encyklopaedie der technischen Chemie, Vol. 12, pp. 398 et seq.) and generally contains from 95 to 70% of methanol, from 1 to 29% of water and from 0.1 to 6% of impurities, by weight. According to manufacture and storage, the impurities may be, for example, alkali metal salts such as sodium formate, sodium hydrogen carbonate, sodium carbonate, sodium acetate, sodium sulfide; sodium and sodium methoxide, potassium hydroxide, sodium hydroxide; formic acid; aldehydes such as acrolein, glyoxal, propionaldehyde and acetaldehyde; ketones such as acetone and butanone-2; glycol and higher alkanols such as isobutanol, isopropanol, n-propanol, isohexanol and isoheptanol; ethers such as dimethyl ether; organic and inorganic compounds such as formates and sulfides of metals such as iron, chromium, copper, aluminum, zinc and magnesium; sulfur compounds such as dimethyl sulfide; esters such as dimethyl terephthalate; amines such as monomethylamine, dimethylamine and trimethylamine; and ammonia. In particular, alkaline impurities are usually present, since the acid present in methanol is neutralized with alkali in nearly all syntheses.

When crude methanol is evaporated, it effervesces vigorously and not only vapors but also liquid and solid impurities are taken up into the vaporous starting mixture for the formaldehyde synthesis, which impurities may be in the form of fine droplets or finely divided solid particles or a mist of liquid. These impurities tend to cause side reactions during the methanol conversion and attack the catalyst, for example by destroying the active surface of the silver or by deposition of solid or resinous particles onto the catalyst and thus shorten the life of the catalyst and reduce the yield of product, which increases the cost of the process. Moreover, deposits may substantially interfere with the operation of the plant by causing blockage of pipes or corrosion of metal surfaces. The catalyst, which consists of silver granules, gradually loses its permeability to gases when covered by the deposits. The loss of pressure across the catalyst bed increases and necessitates higher energy output for air compression. Using the blowers commonly employed, it is then no longer possible to pass the requisite amount of air through the plant so that the conversion rate falls and the plant has to be stopped at an early stage in order to renew the catalyst. This is another cause of losses of yield. In addition, the shorter life of the catalyst increases the cost of changing and regenerating the catalyst.

The apparatus used for evaporating methanol is generally equipped with liquid catchers (B.I.O.S. final report No. 1,331; F.I.A.T. final report No. 999), e.g. packings consisting of Raschig rings or wire netting. Such packings are effective to a certain degree until they reach a stage of saturation. Beyond this point, some of the liquid passed right through the packing and forms droplets or a mist downstream thereof. Thus these measures are not able to prevent extensive deposition of material on the catalyst. For these reasons, it has not hitherto been possible to manufacture formaldehyde from crude methanol on a large scale.

German Pat. Nos. 1,235,881 and 1,136,318 and German Published Application No. 1,277,834 reveal that crude methanol may be used as starting material on a large scale if it is purified by distilling off a low-boiling fraction or if it is treated with alkalis and/or oxidizing agents. These processes dispense with the expensive and time-consuming fractional distillation of the methanol. Despite the advantages of these processes, the life of the catalyst and the yields and space-time yields of pure product produced with said catalyst are still unsatisfactory, as some of the impurities in the crude methanol, particularly the alkaline compounds, are not separated and tend to inactivate the catalyst during the reaction.

Recently, methanol has also been produced by the so-called low-pressure process. In this process, carbon monoxide and hydrogen are converted to methanol at pressures below 150 atmospheres and at temperatures below 300°C. Catalysts used in the low-pressure process are those containing copper, zinc and a third element, e.g. chromium, or a difficultly reducible metal of groups II to IV of the Periodic Table. Such catalysts are described, for example, in U.K. Pat. Nos. 1,010,871 and 1,159,035. German Printed Application No. 1,932,522 recommends that crude methanol coming from the low-pressure process be used for formaldehyde synthesis without any pretreatment. According to the Examples of said printed application, this leads to formaldehyde solutions which contain up to 14% of methanol. The high concentration of unreacted methanol in these aqueous formaldehyde solutions is undesirable for most purposes and necessitates the subsequent removal of the methanol by distillation, which methanol is recycled to the formaldehyde synthesis reaction. It has also been found that the silver catalyst, when unpurified crude methanol from the low-pressure process is used, loses some of its activity after an on-stream period of only 100 hours and the loss of pressure in the reactor progressively increases due to the deposition of solid residues on the catalyst. This makes it necessary to stop the plant and change the catalyst after relatively short on-stream times.

It is an object of the invention to provide a new process for manufacturing formaldehyde in good yield and purity in a simpler and more economical manner.

We have now found that formaldehyde may be manufactured by oxidative dehydrogenation of methanol in the presence of a silver catalyst at elevated temperature in an advantageous manner if the reaction is carried out using crude methanol which is caused to impinge, in vapor form, against baffle plates before entering the catalyst zone, the impurities which separate at said baffle in solid or liquid form being collected.

The process of the invention produces formaldehyde in good yield and purity in a simpler and cheaper manner than prior art processes making use of pure methanol. Compared with syntheses in which crude methanol is used as starting material, formaldehyde is produced by the process of the invention in better yield, space-time yield and purity and with a longer catalyst life. Liquid mists, finely divided solids or droplets of solutions are largely removed. These advantageous results are surprising in view of the prior art.

Suitable starting materials for use in the process are crude methanols prepared by high-pressure or low-pressure processes or, advantageously, mixtures of such crude methanols with water; the concentration of the aqueous mixtures may conveniently be from 60 to 95% and preferably from 70 to 90% of methanol, by weight. In an advantageous embodiment, crude methanol is used such as has been purified by the removal of a low-boiling fraction or by treatment with oxidizing agents and/or alkalis according to German Printed Application No. 1,277,834 and German Pat. Nos. 1,235,881 and 1,136,318. We prefer to use crude methanol which has been treated by the process described in German Pat. No. 1,235,881.

The crude methanol is fed to the reaction chamber in vapor form and advantageously in admixture with steam, recycled off-gas and, if necessary, inert gas. A suitable inert gas for use in the process is, for example, nitrogen.

A suitable oxidizing agent is pure oxygen or a gas with contains elementary oxygen, such as air. The molar ratio of oxygen to crude methanol is conveniently from 0.3 to 0.6:1 and in particular from 0.4 to 0.5:1, while a convenient molar ratio of air to crude methanol is from 1.4 to 2.9:1. Oxidation may, if desired, be carried out in the presence of up to 2 moles and advantageously from 1 to 1.65 moles and in particular from 1.3 to 1.5 moles of off-gas per mole of crude methanol. Preferably, the total amount of water vapor and off-gas added in addition to the air is not more than 3.0 moles per mole of crude methanol.

Any silver catalyst is suitable for use in the process of the invention, for example any of those described in German Printed Application 1,231,229 and Ullmann's Encyklopaedie der technischen Chemie, Vol. 7, pp. 659 et seq. It is preferred to use silver catalysts arranged in two layers, as described for example in German Printed Application No. 1,294,360 and German Laid Open Application No. 1,903,197. For information on the manufacture of the catalyst and the execution of the desired reaction using such catalysts, see the cited publications. A preferred embodiment of the process of the invention comprises effecting the reaction using such a double-layer catalyst of which the lower layer has a thickness of from 15 to 40 mm and in particular from 20 to 30 mm and consists of at least 50% by weight of crystals having a particle size of from 1 to 4 mm and in particular of from 1 to 2.5 mm and of which the upper layer has a thickness of from 0.75 to 3 mm and in particular from 1 to 2 mm and consists of crystals having a particle size of from 0.1 to 1 mm and in particular from 0.2 to 0.75 mm, and loading this catalyst with from 1 to 3 metric tons and in particular from 1.4 to 2.4 tons of methanol per square meter of catalyst bed cross-section per hour. In large-scale work, it is preferred to use catalyst beds having a diameter of at least 0.5 m and conveniently of from 1 to 3 m.

In other respects, oxidation is carried out in known manner by passing a gaseous mixture consisting of crude methanol vapor, air, inert gas (if desired) and, conveniently, off-gas and steam at the rates specified above and at temperatures of from about 550° to 750°C and in particular from 600° to 700°C through said silver catalyst. The process is generally carried out continuously at pressures of from 0.5 to 2 atmospheres and preferably from 0.8 to 1.8 atmospheres. It is advantageous to cool the reaction gases leaving the catalyst zone over a short period, for example in less than one tenth of a second, to temperatures of, say, 350°C. The cooled gaseous mixture is then conveniently passed to an absorption column, in which the formaldehyde is washed out of the gaseous mixture with water, advantageously countercurrently.

A portion of the remaining off-gas is then allowed to escape, while the other portion is conveniently recycled to the reaction. This recycled portion of the off-gas consists of from 1 to 2 moles per mole of crude methanol fed to the reaction. The off-gas essentially contains nitrogen, hydrogen, carbon dioxide, carbon monoxide, water, methanol, argon and usually from 0.1 to 0.5 g of formaldehyde per cubic meter of off-gas. It is conveniently treated with an alkaline compound (advantageously with an amount thereof such that a pH of at least 10 and preferably of from 11 to 13.5 is obtained) and/or oxidizing agents and is then mixed with the other components of the starting mixture and re-fed to the reaction chamber. Suitable alkaline compounds for this are preferably alkalis such as solid or water-dissolved hydroxides, oxides or carbonates or alkali metals or alkaline earth metals or other alkaline materials such as alkali metal alcoholates, and strongly basic and usually high-boiling amines such as triethanolamine. Suitable oxidizing agents are, for example, hydrogen peroxide, sodium peroxide in aqueous solution; perborates and percarbonates, conveniently in admixture with water; potassium permanganate or chromic acid, conveniently in the form of from 0.5 to 10% w/w aqueous solutions. In general, from 0.02 to 10 g of oxidizing agent are used per cubic meter of off-gas. This treatment is generally carried out continuously at a temperature of from 20° to 150°C and at atmospheric or superatmospheric pressures. It is also possible to effect the treatment in two stages, the first stage preferably comprising treatment with the basic compound, while the second stage is the treatment with oxidizing agent. The treatment of the off-gas is preferably carried out using the process described in German Laid Open Application No. 2,022,818.

The shape and material of the baffle plates may be varied over a wide range. For example, plates may be used which are at an angle to or preferably at right angles to the direction of flow of the gaseous mixture and which are made of, say, iron, V2A steel or plastics material such as polyvinyl chloride or polyethylene. The baffle plates may be non-homogeneous, for example they may consist of layers of glass fibers or glass wool. The baffle plates may also be formed by suitable parts of the walls of the equipment through which the gaseous mixture is passed, e.g. the inclined surfaces of a zig-zag pipeline. Conveniently, the baffle plates are provided with pocket-like attachments, e.g. liquid catchers or phase-separating chambers. The droplets or particles of solid material present in the gaseous mixture accumulate at the baffle plates and agglomerate between the separate baffle plates to finally collect in the pocket-like attachments together with liquid methanol and/or water, in which attachments they are retained, separated from the gas stream and led off to appropriate receivers. Obviously, the effect is enhanced by using as many baffle plates or pocket attachments as possible. A preferred embodiment of the process makes use of the flow grid described in Chemie- Ingenieur-Technik, Vol. 39, pp. 1407 et seq. (1967) as baffle plates, in which the gas stream is passed through a number of zig-zag tubes provided with a series of phase-separating chambers in the manner described in said reference. Preferably, the feed pipes have a slot-shaped cross-section. Alternatively, zig-zag baffle plates may be inserted into tubes. The pockets and phase-separating chambers are conveniently disposed at right angles to the direction of flow of the feedstock. If necessary, when using flow grids, some crude methanol may be injected in liquid form into the vapor/air mixture or the baffle walls may be cooled to produce more condensate thereon for washing out the pockets and phase-separating chambers.

The vapor/gas stream comprising the feedstock is generally caused to impinge against the baffle plates at a temperature of from 60° to 100°C. The baffle plates or the flow grid are advantageously maintained at a temperature of from 60° to 250°C and preferably from 75° to 120°C. The stream of vapor and gas conveniently flows at a rate of from 7 to 22 m/s.

In another advantageous embodiment, the catalyst is contained in a vertical reactor of which the top is covered by a hood beneath which there is a circle of from 15 to 40 baffle plates in the form of square segments separated from each other by corresponding square spaces. The arrangement of the circle of baffle plates is conveniently such that the baffle plates themselves form extensions of the wall of the reactor. The lower edge of the baffle plates, which also constitutes the upper edge of the reactor, has liquid catchers attached thereto, these being in the form of inner and outer circular gutters. The gaseous mixture flows through a pipe to impinge against from three to 10 of the baffle plates at right angles thereto, which baffle plates form a segment of the circle of baffle plates. Said feedpipe and the hood form the closure of the top of the reactor. Conveniently, the hood surrounds the circle of baffle plates in such a manner that a suitably dimensioned annular space is formed between the hood and the baffle plates.

The gaseous feedstock flows against the vertical baffle plates, onto which is deposited some condensate (which flows down into the gutters) before passing between the baffle plates and flowing vertically down through the catalyst bed, where the reaction takes place. The resulting reaction mixture flows on down through a cooling zone and is then worked up in the manner described above.

The circular gutters running round the inside and outside of the baffle plates are sufficiently large to accommodate all of the impurities deposited. As the gutters are heated by radiation from the catalyst, the separated water and methanol contained therein evaporate.

The baffle plates may be all of the same size with equal spacing. Preferably, the spaces between the baffle plates are small over that part of the circle which is near the feedpipe inlet and are large over the remaining part of the circle to ensure that the gaseous mixture does not pass through the said spaces substantially on one side of the circle only but is distributed through the annular space surrounding the baffle plates and then flows against the baffle plates on all sides of the circle before passing between them to the catalyst. An advantageous embodiment has for example the following dimensions for a circle of baffle plates having a diameter of 200 cm: width of annular space 20 cm; width of baffle plates near the gas inlet 12 cm; width of interspaces between the baffle plates near the gas inlet 8 cm; width of baffle plates over the part of the circle remote from the gas inlet 8 cm; width of interspaces between the baffle plates remote from the gas inlet 15 cm; number of baffle plates plates 23; width of inner and outer gutters 10 cm each; depth of gutters 15 cm each.

Advantageously, a second circle of baffle plates may be arranged around the first circle of baffle plates, the second set of baffle plates being, conveniently, in staggered relationship to the baffle plates in the first set.

In the case of apparatus comprising baffle plates whose vertical axes are at right angles to the direction of flow, as in the preferred embodiment described above for example, it is preferred to cause the gaseous mixture to impinge against the baffle plates at a rate of from 500 to 3,000 g of crude methanol per second per square meter (of total baffle area) and to operate at a ratio of total baffle area to total interspace area (for the passage of the gaseous mixture) of from 0.4 to 5:1, the number of baffle plates used per meter of the diameter of the feedline being from 25 to 50.

The formaldehyde produced by the process of the invention is valuable as a disinfectant, tanning agent, reducing agent and intermediate in the manufacture of synthetic resins, adhesives and plastics materials. For information on the use of formaldehyde reference is made to the cited volume of Ullmann's Encyklopaedie, p. 670.

In the following Examples the parts are by weight. The yields given are in percent of theory based on the weight of methanol introduced (calculated on a 100% basis).

EXAMPLE 1

The plant used comprises a crude methanol evaporator and a vertical tubular reactor. The reactor is provided at its top with a circle of baffle plates as described above, an inlet for the gaseous feedstock and a hood. The catalyst bed (a bed having a height of 2.6 cm and containing silver granules having a diameter of from 0.4 to 2.5 mm) is situated below the top of the reactor and above a cooling zone. The reactor is connected to an absorption column. The circle of baffle plates has the following data: diameter of circle 200 cm; width of annular space 20 cm; width of baffle plates near the inlet 12 cm; width of interspaces near the inlet 8 cm; width of baffle plates in the part of the circle remote from the inlet 8 cm; width of interspaces remote from the inlet 15 cm; number of baffle plates 23; width of the inner and outer gutters 10 cm each; depth of gutters 15 cm each.

A mixture of 3,050 parts/hr of crude methanol (prepared by a high-pressure process and containing 5 parts/hr of sodium hydroxide), 2,050 parts/hr of water and 5,480 parts/hr of air is fed to the evaporator and evaporated therein. 81 parts/hr of residue, of which more than 95% by weight consists of water, are withdrawn. The mixture of methanol vapor, water vapor and air and containing a mist of salt and liquid (at 78°C) is caused to impinge against the baffle walls (90°C) of the reactor at a rate of flow of 9.2 m/s. The finely divided solid particles or liquid droplets in the gaseous mixture are deposited on the baffle plates and are washed down into the gutters. A crust consisting of 4.2 parts of solid material forms in the gutters over a period of 1,920 hours. The solid deposit has the following composition: 22% of sodium formate, 77% of sodium carbonate, 0.5% of sodium bicarbonate, 0.01% of sulfur compounds, 0.01% of magnesium compounds, 0.01% of aluminum compounds, 0.02% of iron compounds, 0.01% of copper compounds, 0.005% of silicon compounds, 0.01% of calcium compounds and 0.01% of lead compounds, by weight. The purified feedstock is passed through the catalyst (153 parts) and reacted at 690°C under a pressure of 1.3 atmospheres. The reaction mixture is then cooled to 150°C and dissolved in water. The off-gases consist of 0.05% of formaldehyde, 6.3% of steam, 1.2 % of hydrogen, 0.3% of carbon monoxide, 7.2% of carbon dioxide and 84.9% of nitrogen, by weight. There are obtained 3,150 parts/hour of formaldehyde (calculated on a 100% basis) in the form of a 40.2% w/w formaldehyde solution. This is equivalent to a yield of 82.5% of theory. The life of the catalyst is 80 days. After an on-stream period of 1,920 hours, only slight traces of salt deposits (0.08 part) are found on the catalyst.

EXAMPLE 2

Example 1 is repeated but without the use of the system of baffle plates. The catalyst is contaminated with 2.3 parts of salt deposits and the life of the catalyst is 28 days. The yield is 81.6% of theory.

EXAMPLE 3

Example 1 is repeated using an additional set of similar baffle plates of steel plus 12 phase-separating chambers. The apparatus is essentially the same as the flow grid described in Chemie-Ingenieur-Technik, Vol. 39, pp. 1107 et seq. (1967). No salt deposit is found on the catalyst and the life of the catalyst is 80 days. The yield is 82.4% of theory.

EXAMPLE 4

Example 1 is repeated using an additional system of eight baffle plates inserted between the inlet for the feedstock and the original circle of baffle plates such that eight of the interspaces between baffle plates of the original group are covered by the eight baffle plates in the additional group so that they are in the shadow of said additional plates. The distance between the groups of baffle plates is 18 cm. The baffle plates are all of the same size. No deposit is found on the catalyst. The life of the catalyst is 81 days and the yield is 82.2% of theory.

EXAMPLE 5

Example 1 is repeated using a low-pressure crude methanol which has been prepurified by the method described in German Pat. No. 2,034,532. No deposit is found on the catalyst. The life of the catalyst is 70 days and the yield, based on methanol, is 82.90% of theory.

EXAMPLE 6

The same equipment is used as in Example 1, and a mixture of 3,058 parts of crude methanol (prepared in a high-pressure process), 782 parts of water, 3,475 of recycled off-gas (which has been washed with a 2% w/w aqueous sodium peroxide solution), 5 parts of sodium hydroxide and 5,490 parts of air is fed to the evaporator per hour and evaporated therein. 70 parts/hr of residue, of which more than 95% by weight consists of water, are withdrawn. Over an on-stream period of 768 hours a crust is formed in the gutters consisting of 5.2 parts of solid material. This material consists of 25% of sodium formate, 74% of sodium carbonate, 0.5% of sodium bicarbonate, 0.01% of sulfur compounds, 0.01% of magnesium compounds, 0.01% of aluminum compounds, 0.02% of iron compounds, 0.01% of copper compounds, 0.005% of silicon compounds, 0.01% of calcium compounds and 0.01% of lead compounds, by weight.

The life of the catalyst is 75 days. At this point, only slight traces of salt deposits (0.01 part) are found on the catalyst. The yield, based on methanol, is 82.72% of theory.

We claim:

1. In a process for the manufacture of formaldehyde by oxidative dehydrogenation of methanol in the presence of a silver catalyst at elevated temperature, the improvement comprising carrying out the reaction using crude methanol which is caused to impinge in vapor form against baffle plates before entering the catalyst zone, the impurities which separate at said baffle plates in solid or liquid form being collected.

2. A process as claimed in claim 1, wherein the reaction is carried out at a molar ratio of crude methanol to air of 1:1.4 to 1:2.9.

3. A process as claimed in claim 1, wherein the reaction is carried out using a double-layer catalyst, of which the lower layer has a thickness of from 15 to 40 mm and consists of at least 50% by weight of crystals having a particle size of from 1 to 4 mm, and of which the upper layer has a thickness of from 0.75 to 3 mm and consists of crystals having a particle size of from 0.1 to 1 mm, the space velocity being from 1 to 3 metric tons of methanol per $m^2$ of catalyst bed cross-section per hour.

4. A process as claimed in claim 1, wherein the reaction is carried out using a gas mixture consisting of crude methanol vapor, air, off-gas and water vapor.

5. A process as claimed in claim 1, wherein the reaction is carried out at a temperature of from 550° to 750°C.

6. A process as claimed in claim 1, wherein the reaction is carried out at a temperature of from 600° to 700°C.

7. A process as claimed in claim 1, wherein the reaction is carried out at pressures between 0.5 and 2 atmospheres.

8. A process as claimed in claim 1, wherein the reaction is carried out using a circle of from 15 to 40 baffle plates in the form of square segments with corresponding square spaces therebetween.

9. A process as claimed in claim 1, wherein the reaction is carried out at a rate of flow of from 500 to 3,000 g/s of crude methanol impinging against the baffle plates per square meter of their total area and at a ratio of square meters of total baffle area to square meters of total interspace area (for the passage of the gaseous mixture) of from 0.4:1 to 5:1, the number of baffle plates being from 25 to 50 per meter of diameter of the feedline.

* * * * *